United States Patent [19]
Astles et al.

[11] Patent Number: 5,158,599
[45] Date of Patent: Oct. 27, 1992

[54] SULPHONAMIDE HERBICIDES

[75] Inventors: David P. Astles, Rainham; Andrew Flood, Cowley; Trevor W. Newton, Sittingbourne; David C. Hunter, Cambridge, all of England

[73] Assignee: Shell Research Limited, United Kingdom

[21] Appl. No.: 557,720

[22] Filed: Jul. 26, 1990

[30] Foreign Application Priority Data

Jul. 31, 1989 [GB] United Kingdom ............. 8917476

[51] Int. Cl.$^5$ ............. C07D 239/34; C07D 239/52; C07D 239/60; A01N 43/54
[52] U.S. Cl. .................................. 71/92; 71/90; 544/300; 544/301; 544/310; 544/311; 544/312; 544/316; 544/317
[58] Field of Search ............ 71/92, 90; 544/300, 544/301, 310, 311, 312, 316, 317

[56] References Cited

FOREIGN PATENT DOCUMENTS 347811 12/1989 European Pat. Off. .

Primary Examiner—John M. Ford

[57] ABSTRACT

Compounds of the formula

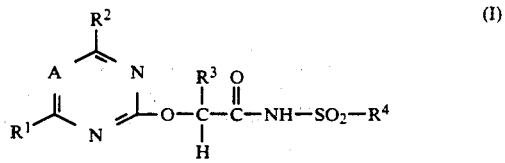

in which
A is nitrogen or $CR^5$;
$R^1$, $R^2$ and $R^5$ each independently are hydrogen, or halogen, formyl, cyano, carboxy or azido, or optionally substituted alkyl, alkenyl, alkynyl, cycloalkyl, alkoxy, alkenyloxy, alkynyloxy, aryloxy, alkylthio, alkenylthio, alkynylthio, arylthio, alkylcarbonyl, alkoxycarbonyl, amino, aminoxy or dialkyliminoxy;
$R^3$ is a hydrogen, or optionally substituted alkyl, alkenyl, alkynyl, cycloalkyl, heterocyclic, aralkyl or aryl; and
$R_4$ optionally substituted alkyl, aralkyl, aryl or heterocyclyl; and salts thereof, have herbicidal properties. The invention also provides processes for their preparation and their use as herbicides.

9 Claims, No Drawings

SULPHONAMIDE HERBICIDES

The present invention relates to sulphonamide derivatives, processes for their preparation and their use as herbicides.

Sulphonamide compounds are well known for their biological activity. Certain classes of sulphonamide derivatives are useful as herbicides whilst other classes are useful as anti-bacterial agents.

A structurally distinct class of sulphonamide derivatives has now been found which have useful herbicidal properties.

The present invention provides a compound of the general formula

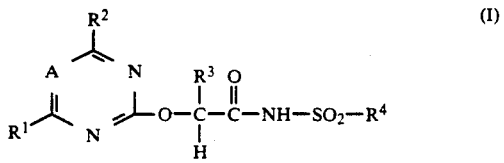

in which

A represents a nitrogen atom or a group $C^5$;

$R^1$, $R^2$ and $R^5$ each independently represents a hydrogen or halogen atom, a formyl, cyano, carboxy or azido group, or an optionally substituted alkyl, alkenyl, alkynyl, cycloalkyl, alkoxy, alkenyloxy, alkynyloxy, aryloxy, alkylthio, alkenylthio, alkynylthio, arylthio, alkylcarbonyl, alkoxycarbonyl, amino, aminoxy or dialkyliminoxy group;

$R^3$ represents a hydrogen atom, or an optionally substituted alkyl, alkenyl, alkynyl, cycloalkyl, heterocyclic, aralkyl or aryl group; and $R^4$ represents an optionally substituted alkyl, aralkyl, aryl or heterocyclic group;

or a salt thereof.

An alkyl, alkenyl or alkynyl radical or moiety may be a straight or branched chain group. Generally an alkyl radical or moiety has from 1 to 12 carbon atoms, preferably from 1 to 6, especially from 1 to 4, carbon atoms. Alkenyl and alkynyl radicals or moieties suitably have from 2 to 12 carbon atoms, preferably from 2 to 6, especially from 2 to 4, carbon atoms. Cycloalkyl groups suitably have from 3 to 8 carbon atom ring members.

An aryl radical, or an aryl moiety in an aralkyl, aryloxy or arylthio radical, may be a single or fused carbocyclic ring system having from 6 to 10 ring members. Suitably an aryl radical or moiety comprises a single ring system and preferably is a phenyl ring.

A heterocyclic radical is suitably a single or fused, saturated or unsaturated ring system having from 5 to 10, preferably 5 or 6, ring members of which from 1 to 3 ring members may be hetero atoms selected from oxygen, nitrogen and sulphur atoms.

Radicals represented by the symbols $R^1$, $R^2$, $R^3$, $R^4$ and $R^5$ may be unsubstituted or substituted. Where substituents are present, the substituent groups may be any of those customarily employed in the modification and/or development of pesticidal compounds and are especially substituents that maintain or enhance the herbicidal activity associated with the compounds of the present invention, or influence persistence of action, soil or plant penetration, or any other desirable property for herbicidal compounds. There may be one or more of the same or different substituents present in each radical.

Optional substituents for alkyl, alkenyl, alkynyl, alkoxy, alkenyloxy, alkynyloxy, alkylthio, alkenylthio, alkynylthio, alkylcarbonyl alkoxycarbonyl groups or alkyl moieties in aralkyl groups may be independently selected from one or more of halogen atoms and alkoxy, alkenyloxy, aryloxy, hydroxy, alkylthio, arylthio, aryl, alkylsulphonyl, alkylsulphinyl, alkylenedioxy, alkylenedithio, haloalkyl and alkoxycarbonyl groups, heterocyclic groups, and dialkyliminoxy, optionally substituted amino, trialkylsilyl, alkylcarbonyl, arylcarbonyl, alkoxycarbonyl, carboxy, cyano, thiocyanato and optionally substituted aminocarbonyl groups.

Optional substituents for aryl, cycloalkyl aryloxy or arylthio groups, heterocyclic rings or aryl moieties in aralkyl groups may be independently selected from one or more of halogen atoms and nitro, cyano, alkyl, haloalkyl, alkoxy, haloalkoxy, alkylthio, alkylsulphonyl, mono- or di-alkylsulphonamido, aryloxy, carboxy, alkoxycarbonyl and aralkoxycarbonyl groups.

Optional substituents for an amino group or for an amino moiety in an aminoxy or aminocarbonyl group, may suitably be independently selected from alkyl, alkenyl, aryl, alkoxy, amino, mono- or di-alkylamino, arylamino, alkoxyalkyl, haloalkyl, hydroxy, hydroxyalkyl, cyano, carboxyalkyl or alkylcarbonylamino, or the amino group may form part of a heterocyclic ring.

Suitable salts of the invention are agrochemically acceptable salts of compounds of general formula I. It is possible for salts to be formed with inorganic or organic cations by conventional methods. Such salts suitably include salts with inorganic cations derived from alkali metals and alkaline earth metals such as, for example, sodium, potassium, calcium and magnesium, and from transition metals, for example copper, and salts with organic cations such as alkylammonium and alkylsulphonium cations.

An alkyl radical or moiety when present as a substituent or as part of a substituent group, preferably has from 1 to 4 carbon atoms, especially 1 or 2 carbon atoms. A haloalkyl or haloalkoxy radical suitably has from 1 to 3 halogen atoms; a preferred haloalkyl radical is a trifluoromethyl group and a preferred haloalkoxy radical is a trifluoromethoxy group. As a substituent, an alkenyl moiety suitably has from 2 to 4 carbon atoms. An aryl radical when present as a substituent is preferably a phenyl group. A halogen atom as a substituent is suitably a fluorine, chlorine or bromine atom.

A is preferably a nitrogen atom or a group CH.

Suitable examples of the radicals $R^1$ and $R^2$ include $C_{1-4}$ alkyl groups and $C_{1-4}$ alkoxy groups. Preferably $R^1$ and $R^2$ are independently selected from methyl groups and methoxy groups.

Suitable examples of the radical $R^3$ include hydrogen, optionally substituted $C_{1-6}$ alkyl, $C_{2-6}$ alkenyl, $C_{2-6}$ alkynyl, $C_{3-6}$ cycloalkyl, phen($C_{1-4}$)alkyl, suitably benzyl, and phenyl groups, and 5 or 6 membered heterocyclic groups. Preferably the radical $R^3$ is selected from hydrogen atoms, $C_{1-4}$ alkyl groups and phenyl groups.

Suitably, the radical $R^4$ is a $C_{1-6}$ alkyl group or an optionally substituted phenyl or benzyl group, or a thienyl group. Preferably, $R^4$ represents a $C_{1-4}$ alkyl group, especially a methyl group, an unsubstituted phenyl group or a phenyl group substituted by one or more, preferably 1 or 2, of the same or different substituents selected from halogen atoms, nitro groups and $C_{1-4}$ alkyl, $C_{1-4}$ haloalkyl, $C_{1-4}$ haloalkoxy, carboxy and ($C_{1-4}$ alkoxy)carbonyl groups. Especially preferred substituents are fluorine, chlorine, bromine, nitro, methyl, trichloromethyl, trifluoromethoxy and methoxycarbonyl.

It will be appreciated that the compounds of the present invention in which $R^3$ is other than a hydrogen atom have an asymmetric carbon atom and will therefore exist in different stereoisomeric forms. The present invention accordingly includes all individual isomeric forms of the compounds of general formula I and mixtures thereof in whatever proportion. Thus, the R- and S-enantiomers of the compound of general formula IA

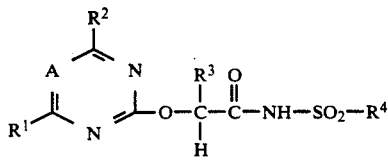
(IA)

in which A, $R^1$, $R^2$ and $R^4$ are as hereinbefore defined and $R^3$ is other than a hydrogen atom, and mixtures thereof, are included within the present invention.

The present invention further provides a process for the preparation of a compound of the present invention, which process comprises (a) reacting a compound of the general formula

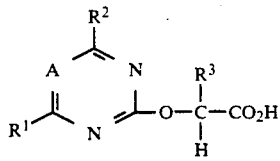
(II)

in which A, $R^1$, $R^2$ and $R^3$ are as defined above, or a corresponding ester, acid chloride or acid anhydride, with a compound of the general formula

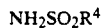 (III)

in which $R^4$ is as previously defined, or a salt thereof, if appropriate in the presence of a carboxyl-activating agent, or (b) reacting a compound of the general formula

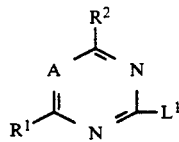
(IV)

in which A, $R^1$ and $R^2$ are as previously defined and $L^1$ represents a leaving group, with a di-salt of a compound of the general formula

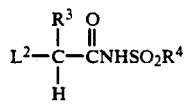
(V)

in which $R^3$ and $R^4$ are as previously defined and $L^2$ represents a hydroxy group, and, if required or desired, converting a resulting compound into any other compound of the invention.

A leaving group is any group that will, under the reaction conditions, cleave from the starting material thus promoting reaction at a specified site.

The leaving group in a compound of general formula IV is conveniently a halogen atom, for example a bromine, chlorine or iodine atom, or, especially for the pyrimidine starting materials, an alkanesulphonyl group, for example methanesulphonyl.

A di-salt of compound V is suitably a di(alkali metal) salt, preferably a di-sodium salt.

Process (a) is suitably carried out at ambient or elevated temperature, i.e. at a temperature above 20° C. A preferred temperature range in which to carry out the reaction is from 20° C. to 80° C.; an especially suitable reaction temperature is in the range of from 20° C. to 50° C. The molar ratio of reactant II to reactant III may, for example, be in the range of from 1.0 to 5.0 preferably from 1.0 to 2.5.

The reaction (a) is suitably carried out in an inert organic solvent such as a hydrocarbon solvent, e.g. benzene or toluene, a chlorinated hydrocarbon, e.g. dichloromethane or chloroform, an alcohol, e.g. methanol or ethanol, an ether, e.g. diethyl ether, tetrahydrofuran, 1,4-dioxane, a ketone, e.g. acetone or methyl ethyl ketone, an ester, e.g. ethyl acetate, an aprotic polar solvent, e.g. dimethylformamide, dimethylacetamide or dimethylsulphoxide or a nitrile, e.g. acetonitrile.

Preferably, the reaction (a) is carried out in the presence of a tertiary amine, for example triethylamine. Other suitable tertiary amines include pyridine and 1,8-diazabicyclo[5.4.0]undec-7-ene.

When the reactant II is in the form of a free carboxylic acid, the carboxy group needs to be activated for the reaction to proceed. Suitable carboxyl-activating agents include 2-chloro-N-methyl pyridinium iodide, dicylohexylcarbodiimide and carbonyldiimidazole. Suitably the acid reactant II is activated by the carboxyl-activating agent in the presence of an inert organic solvent at ambient or elevated temperature, for example at a temperature in the range of from 20° C. to the reflux temperature of the mixture, prior to the addition of reactant III and, if desired, the tertiary amine.

Process (b) is suitably carried out at a temperature in the range of from ambient to the reflux temperature of the reaction medium, preferably in the range of from 100° to 150° C., for example at 120° C. The molar ratio of the reactants IV:V is suitably in the range of from 10 to 2.5.

In reaction (b) the di-salt may suitably be prepared from a compound V in which $L^2$ is a hydroxy group by the action of an alkali metal, such as metallic sodium or potassium, or, conveniently, a strong base, for example, an alkali metal hydride, such as sodium or potassium hydride, an alkaline earth metal hydride, such as calcium hydride, an alkali metal alkoxide, such as potassium t-butoxide, or an alkali metal hydroxide, such as sodium or potassium hydroxide. Suitably conversion of a hydroxy compound V to the di-salt occurs in situ.

Suitably, the reaction (b) is carried out in the presence of a solvent; typical solvents are, for example, the same as noted above for process (a).

The compound of general formula I obtained by either of the methods (a) or (b) may be converted to a further compound of general formula I by methods known to a man skilled in the art, provided that suitable care is taken to ensure that the sulphonamide group is not affected. Thus for example, a compound of general formula I where $R^1$ and/or $R^2$ represents a halogen atom, suitably chlorine, may be transformed into other derivatives by nucleophilic displacement, for example by reaction with two equivalents of an amine, such as dimethylamine, to give the corresponding compound of general formula I in which $R^1$ and/or $R^2$ represents a substituted amino group. Likewise a compound of general formula I in which $R^1$ and/or $R^2$ represents a halogen atom, may be reacted with two equivalents of an alkylthio organo-metallic compound, for example sodium methanethiolate, to yield the corresponding compound of general formula I in which $R^1$ and/or $R^2$ represents an alkylthio group such as methylthio, or may be hydrogenated to yield the corresponding compound in which $R^1$ and/or $R^2$ is a hydrogen atom.

Acid and salt conversion reactions may be carried out using conventional techniques as appropriate.

Individual enantiomers may be obtained using stereospecific reactants or by conventional resolution techniques.

The prepared compounds of the invention may, if desired, be isolated and purified using conventional techniques.

Suitable starting carboxylic acids of general formula II, and esters thereof, and also their preparation, are described and claimed in European Patent Application No. 90201334.1. Thus the starting carboxylic acids of general formula II, and esters thereof, may be prepared either by reacting a compound of the general formula

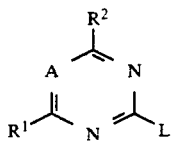

VI in which $R^1$, $R^2$ and A are as defined above and L represents a leaving group, for example a halogen atom or alkanesulphonyl group, with a compound of the general formula

VII in which $R^3$ is as defined above, or an ester thereof, or for compounds in which A represents $CR^5$, reacting a compound of the general formula

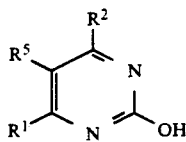

VIII in which $R^1$, $R^2$ and $R^5$ are as defined above, preferably with an ester of a compound of the general formula

IX in which $R^3$ is as defined above and X represents a leaving group, for example a halogen atom or a sulphonyloxy group, and, if required or desired, converting the resulting ester into another ester or into a corresponding acid, or converting an acid into another acid or into an ester. The acid chloride and acid anhydride derivatives are preparable from the compounds of formula II by standard techniques.

The reactants of general formula III are either known or can be prepared using techniques described in the literature.

The starting triazine compounds of general formulae IV and VI (i.e. in which A is a nitrogen atom) are either known or can be prepared using techniques described in the literature. For example such compounds may be prepared from 2,4,6-trichlorotriazine by methods such as those described by Dudley et al, J. Am. Chem. Soc., 73, 2986, (1951), Koopman et al, Rec. Trav. Chim., 79, 83, (1960), Hirt et al, Helv. Chim. Acta, 33, 1365, (1950), Kobe et al, Monatshefte fur Chemie, 101, 724, (1970) and Ross et al, U.S. Pat. No. 3 316 263.

The starting pyrimidines of general formulae IV and VIII may be prepared by conventional techniques, for example those described in Heterocyclic compounds, 16 "The Pyrimidines", edited by D. J. Brown, Interscience, 1962.

The compounds of general formula V may be prepared from the corresponding benzyloxy derivatives

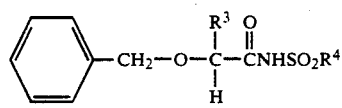

by hydrogenation, suitably using gaseous hydrogen in conjunction with a palladium- or platinum- carbon catalyst. The benzyloxy derivatives may be prepared in analogous fashion to reaction (a) above by the reaction of an appropriate 2-benzyloxycarboxylic acid

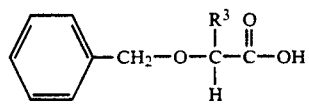

or reactive derivative thereof, with a compound of general formula III described above, or a salt thereof.

The compounds of general formula VII are either known compounds or may be prepared by conventional procedures. Compounds in which $R^3$ represents an aryl group may for example be prepared by treating the corresponding aldehyde, $R^3CHO$, with a suitable cyanide compound, for example potassium cyanide or trimethylsilylcyanide with, respectively, zinc iodide or sodium bisulphite, followed by conversion of the cyano substituent to the acid group, see, for example, Schnur and Morville, J. Med. Chem. 29, 770 (1986) and U.S. Pat. No. 4 537 623. Compounds in Which $R^3$ represents an alkyl group may, for example, be prepared by the method of Kolasa and Miller, J. Org. Chem. 52, 4978, (1987), starting from a suitable amino acid with a 2 stage conversion.

The compounds of general formula IX may be prepared by conventional techniques, for example by halogenating a corresponding compound, for example by the procedure of Epstein et al. J. Med. Chem., 24, 481, (1981).

Compounds of the general formula I have been found to have interesting activity as herbicides having a wide range of pre- and post-emergence activity against undesirable species.

The present invention therefore provides a herbicidal composition which comprises a compound of the present invention in association with a carrier.

Preferably there are at least two carriers in a composition of the present invention, at least one of which is a surface-active agent.

The present invention further provides the use of a compound according to the invention as a herbicide.

Further, in accordance with the invention there is provided a method of combating undesired plant growth at a locus by treating the locus with a compound or composition according to the invention. The locus may, for example, be the soil or plants in a crop area. Application to the locus may be pre-emergence or post-emergence. The dosage of active ingredient used may, for example, be from 0.01 to 10 kg/ha, preferably from 0.05 to 5 kg/ha.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ether; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may also contain other active ingredients, for example, compounds possessing insecticidal or fungicidal properties or other herbicides.

The following Examples illustrate the invention.

EXAMPLE 1

2-(4,6-Dimethylpyrimidin-2-yl)oxy-N-phenylsulphonyl propionamide (a) Methyl 2-(4,6-dimethylpyrimidin-2-yl)oxy propionate 2-Hydroxy-4,6-dimethylpyrimidine (37. 1 g, 0.299 mol) in 500 ml of acetone was brought almost to reflux. 50 g (0.299 mol) of methyl 2-bromopropionate was then added quickly by means of a dropping funnel and potassium carbonate (41.3 g, 0.299 mol) added in portions. The mixture was refluxed overnight. After filtering off the white precipitate, the acetone was removed from the filtrate by evaporation and the crude liquid product was purified by flash column chromatography. 19.6 g (0.093 mol) of the desired compound was obtained as a pale yellow oil.

Yield: 31% by weight.

NMR $\delta(CDCl_3)$:6.57(1H,s), 5.17(1H,q), 3.60(3H,s), 2.25 (6H,s), 1.51 (3H,s) ppm.

(b) 2-(4,6-Dimethylpyrimidin-2-yl)oxypropionic acid

The product of (a) (16.76 g, 0.0798 mol) was dissolved in approximately 150 ml methanol, and about 150 ml of 10% by wt. sodium hydroxide added with stirring. After 30 minutes at room temperature, the methanol was removed by evaporation and the remaining mixture was treated with 10% by wt. hydrochloric acid (pH2). A white solid, the desired product, precipitated out of the solution and was isolated by filtration. The solid was further purified by trituration with diethyl ether. After drying, the total yield of desired product obtained by this procedure was approximately 100% by weight (16.06 g, 0.082 mol of the title compound).

Melting point: 117° C.

(c)
2-(4,6-Dimethylpyrimidin-2-yl)oxy-N-phenylsulphonyl propionamide

Triethylamine (2.84 g, 0.028 mol) was added to 2.00 g (0.0102 mol) of the product of (b) in dry acetonitrile (100 ml) and then, at 50° C., 3.00 g, 0.0118 mol, of 2-chloro-N-methyl pyridinium iodide was also added. The mixture was stirred at 50° C. for 30 minutes and then 3.32 g (0.0212 mol) of benzene sulphonamide and 1.42 g (0.014 mol) of triethylamine were added and the stirring continued at 50° C. for a further 30 minutes. The mixture was allowed to cool to ambient temperature (~20° C.) and left overnight, stirring being maintained for the entire period. The acetonitrile was then removed by evaporation, 50 ml of water added, the mixture acidified to a pH of 2, 50 ml of diethyl ether added and the solution vigorously stirred for 1 hour. The desired product, a beige solid, formed and was filtered off and dried.

2.13 g of the title compound was obtained, a yield of 62% by weight.

Melting point: 188.0° C.

| Elemental Analysis (%): | | | |
|---|---|---|---|
| Calculated | C 53.7 | H 5.1 | N 12.5 |
| Found | C 53.8 | H 5.1 | N 12.4 |

EXAMPLES 2 to 25

The following compounds of the general formula I were prepared in analogous manner to that described in Example 1 above. Analytical and physical data are given in Table I below. An asterisk by a melting point in Table I denotes "with decomposition". The n.m.r. determination given for Examples 11, 12 and 15 was carried out in $d_6$-acetone and not in deuteriochloroform ($CDCl_3$).

TABLE I

| Example No. | A | $R^1$ | $R^2$ | $R^3$ | $R^4$ | Melting Point (°C.) | NMR δ ($CDCl_3$)/ppm or Analysis (%) Calc. Found | | |
|---|---|---|---|---|---|---|---|---|---|
| | | | | | | | C | H | N |
| 2 | CH | $CH_3$ | $CH_3$ | H | $C_6H_5$ | 194.5 | 52.3<br>52.3 | 4.7<br>4.6 | 13.1<br>13.2 |
| 3 | CH | $CH_3$ | $CH_3$ | $C_2H_5$ | $C_6H_5$ | 177.5 | 55.0<br>54.9 | 5.4<br>5.7 | 12.0<br>12.0 |
| 4 | CH | $CH_3$ | $CH_3$ | H | (2-Cl)$C_6H_4$ | oil | 2.24(6H,s), 4.77 (2H,s), 5.75(1H,s), 6.55(1H,s), 7.25 (2H,m), 7.42(1H,m), 8.00(1H,m) | | |
| 5 | CH | $CH_3$ | $CH_3$ | $CH_3$ | (2-Cl)$C_6H_4$ | 188.5* | 48.7<br>48.9 | 4.3<br>4.5 | 11.4<br>11.4 |
| 6 | CH | $CH_3$ | $CH_3$ | $C_2H_5$ | (2-Cl)$C_6H_4$ | 191.8* | 50.1<br>49.7 | 4.7<br>4.8 | 10.95<br>10.8 |
| 7 | CH | $CH_3$ | $CH_3$ | $CH_3$ | (2-$CO_2CH_3$)$C_6H_4$ | 134.0 | 1.55(3H,d), 2.23 (6H,s), 3.84(3H,s), 5.22(1H,q), 6.65 (1H,s), 7.66(3H,m), 8.33(1H,m), 9.5 (1H,broad) | | |
| 8 | CH | $CH_3$ | $CH_3$ | $CH_3$ | (2,5-diCl)$C_6H_3$ | oil | 1.56(3H,d), 2.31 (6H,s), 5.39(1H,q), 6.64 (1H,s), 7.3(2H,m), 8.05 (1H,m) | | |
| 9 | CH | $CH_3$ | $CH_3$ | $CH_3$ | (3-Cl)$C_6H_4$ | 184.0 | 48.7<br>48.7 | 4.3<br>4.6 | 11.4<br>11.5 |
| 10 | CH | $CH_3$ | $CH_3$ | $CH_3$ | (2-$NO_2$)$C_6H_4$ | 174.5 | 47.4<br>47.4 | 4.2<br>4.4 | 14.7<br>14.8 |
| 11 | CH | $CH_3$ | $CH_3$ | $CH_3$ | (2,6-diCl)$C_6H_3$ | 168.5 | 1.48(3H,d), 2.24 (6H,s), 5.20(1H,q), 6.74(1H,s), 7.47 (3H,m) | | |
| 12 | CH | $CH_3$ | $CH_3$ | $CH_3$ | (2,3-diCl)$C_6H_3$ | 172.0 | 1.47(3H,d), 2.20 (6H,s), 5.14(1H,q), 6.73(1H,s), 7.45 (1H,t), 7.75(1H,d), 8.12(1H,d) | | |
| 13 | CH | $CH_3$ | $CH_3$ | $CH_3$ | (4-Cl)$C_6H_4$ | 75.0 | 1.48(3H,d), 2.30 (6H,s), 5.36(1H,q), 6.67(1H,s), 7.40 (2H,m), 7.88(2H,m) | | |
| 14 | CH | $CH_3$ | $CH_3$ | $CH_3$ | (3-$NO_2$)$C_6H_4$ | 165.0* | 1.54(3H,d), 2.35 (6H,s), 5.42(1H,q), 6.75(1H,s), 7.76 (1H,t), 8.46(2H,q), 8.80(1H,s) | | |
| 15 | CH | $CH_3$ | $CH_3$ | $CH_3$ | (4-$NO_2$)$C_6H_4$ | 150.0 | 1.41(3H,d), 2.16 (6H,s), 5.12(1H,q), 6.68(1H,s), 8.10 (2H,d), 8.26(2H,d) | | |
| 16 | CH | $CH_3$ | $CH_3$ | $CH_3$ | (2-$CH_3$)$C_6H_4$ | 206.0 | 55.0<br>55.0 | 5.5<br>5.5 | 12.0<br>11.9 |
| 17 | CH | $CH_3$ | $CH_3$ | $CH_3$ | (2-$CF_3$)$C_6H_4$ | 105.0 | 47.6<br>47.5 | 4.0<br>4.0 | 10.4<br>10.3 |
| 18 | CH | $CH_3$ | $CH_3$ | $CH_3$ | (2-F)$C_6H_4$ | 198.0 | 51.0<br>50.2 | 4.5<br>4.6 | 11.9<br>11.6 |

TABLE I-continued

| Example No. | A | $R^1$ | $R^2$ | $R^3$ | $R^4$ | Melting Point (°C.) | NMR δ (CDCl$_3$)/ppm or Analysis (%) Calc. Found | | |
|---|---|---|---|---|---|---|---|---|---|
| | | | | | | | C | H | N |
| 19 | CH | CH$_3$ | CH$_3$ | CH$_3$ | (2-Br)C$_6$H$_4$ | 89.0 | 1.4(3H,d) 2.2 (6H,s), 5.05(1H,q), 6.8(1H,s), 7.4–8.1 (4H,m), 12.9 (1H,s broad) | | |
| 20 | CH | CH$_3$ | CH$_3$ | CH$_3$ | (2-OCF$_3$)C$_6$H$_4$ | 155.0 | 45.8 45.4 | 3.8 3.7 | 10.0 9.9 |
| 21 | CH | CH$_3$ | CH$_3$ | CH$_3$ | (3-CH$_3$)C$_6$H$_4$ | 189.5 | 55.0 54.7 | 5.4 5.7 | 12.0 11.7 |
| 22 | CH | CH$_3$ | CH$_3$ | CH$_3$ | CH$_3$ | 159.5 | 43.9 43.1 | 5.5 5.5 | 15.4 14.4 |
| 23 | CH | OCH$_3$ | OCH$_3$ | C$_6$H$_5$ | CH$_3$ | 152.5 | 49.0 48.3 | 4.7 4.7 | 11.4 11.1 |
| 24 | CH | OCH$_3$ | OCH$_3$ | C$_6$H$_5$ | C$_6$H$_5$ | 176.0 | 55.9 56.0 | 4.5 4.7 | 9.8 9.9 |
| 25 | CH | CH$_3$ | CH$_3$ | iC$_3$H$_7$ | C$_6$H$_5$ | 128.0 | 56.2 55.9 | 5.8 5.8 | 11.6 11.2 |
| 26 | CH | CH$_3$ | CH$_3$ | CH$_3$ | (2-CO$_2$CH$_3$)C$_6$H$_4$ (R) | 137.3 | 51.9 52.4 | 4.8 5.1 | 10.7 10.9 |
| 27 | CH | CH$_3$ | CH$_3$ | CH$_3$ | (2-CO$_2$CH$_3$)C$_6$H$_4$ (S) | 130.5 | 51.0 52.3 | 4.8 5.3 | 10.7 10.7 |

EXAMPLE 28

2-(4,6-dimethoxyprimidin-2-yl)oxy-N-(methylsulphonyl)propionamide

To a solution of 1,1-carbonyldiimidazole (1.70 g, 0.0105 mol) in dry tetrahydrofuran (130 ml), 2-(4,6-dimethoxypyrimidin-2-yl)oxypropionic acid (2.28 g, 0.01 mol), prepared as described in Example 1(b) above, in tetrahydrofuran (30 ml) was added dropwise at room temperature (~20° C.). The solution was refluxed for ½ hour and allowed to cool. Methanesulphonamide (0.95 g, 0.01 mol) was added in one solid portion and the mixture stirred for 15 minutes before 1,8-diazabicyclo[5.4.0]undec-7-ene (1.52 g, 0.01 mol) in tetrahydrofuran (30 ml) was added dropwise at room temperature (~20° C.). After a short duration the tetrahydrofuran was removed and the residue acidified with 1M hydrochloric acid solution. The product was extracted with chloroform, backwashed with water and dried. The solvent was removed and the product purified on silica gel eluting with 3% by volume methanol/chloroform to yield the title compound as a solid (1.79 g).

Yield: 50% by weight.

Melting point: 178.0° C. Elemental Analysis (%):

| | Elemental Analysis (%): | | |
|---|---|---|---|
| Calculated | C 39.4 | H 4.9 | N 13.8 |
| Found | C 38.5 | H 4.8 | N 13.0 |

Examples 29 to 59

Further compounds of the general formula I were prepared in analogous manner to the procedure described in Example 28. Details of the compounds prepared are given in Table II below.

TABLE II

| Example No. | A | $R^1$ | $R^2$ | $R^3$ | $R^4$ | Melting Point (°C.) | NMR δ (d$_6$-acetone)/ppm or Analysis (%) Calc. Found | | |
|---|---|---|---|---|---|---|---|---|---|
| | | | | | | | C | H | N |
| 29 | CH | OCH$_3$ | OCH$_3$ | C$_6$H$_5$ | C$_2$H$_5$ | 157.0–158.0 | 50.4 50.8 | 5.0 5.2 | 11.0 11.3 |
| 30 | CH | OCH$_3$ | OCH$_3$ | C$_6$H$_5$ | iC$_3$H$_7$ | 168.0–168.5 | 51.7 51.8 | 5.3 5.4 | 10.6 10.9 |
| 31 | CH | OCH$_3$ | OCH$_3$ | C$_6$H$_5$ | (2-CO$_2$CH$_3$)C$_6$H$_4$ | 189.0 | 54.2 54.2 | 4.3 4.4 | 8.6 8.8 |
| 32 | CH | OCH$_3$ | OCH$_3$ | C$_6$H$_5$ | nC$_4$H$_9$ | 153.0–154.0 | 52.8 52.7 | 5.6 5.8 | 10.3 10.4 |
| 33 | CH | OCH$_3$ | OCH$_3$ | C$_6$H$_5$ | CH$_2$C$_6$H$_5$ | 170.0 | 56.9 57.9 | 4.8 4.9 | 9.5 9.3 |
| 34 | CH | OCH$_3$ | OCH$_3$ | C$_6$H$_5$ | (2-Cl)C$_6$H$_4$ | 156.0–157.0 | 51.8 52.3 | 3.9 3.9 | 9.2 9.2 |
| 35 | CH | OCH$_3$ | OCH$_3$ | CH$_2$C$_6$H$_5$ | (2-CO$_2$CH$_3$)C$_6$H$_4$ | 146.0 | 55.1 55.5 | 4.6 4.8 | 8.4 8.7 |
| 36 | CH | OCH$_3$ | OCH$_3$ | CH$_2$C$_6$H$_5$ | C$_6$H$_5$ | 179.0–181.0 | 56.9 56.5 | 4.8 4.3 | 9.5 9.3 |
| 37 | CH | OCH$_3$ | OCH$_3$ | CH$_2$C$_6$H$_5$ | CH$_3$ | 147.0–148.0 | 50.4 50.8 | 5.0 5.2 | 11.0 11.3 |
| 39 | CH | OCH$_3$ | OCH$_3$ | C$_6$H$_5$ | (4-CH$_3$)C$_6$H$_4$ | 165.0 | 56.9 56.3 | 4.8 4.8 | 9.5 9.6 |
| 39 | CH | OCH$_3$ | OCH$_3$ | C$_6$H$_5$ | (4-NO$_2$)C$_6$H$_4$ | 169.0 | 50.6 49.0 | 3.8 4.3 | 11.8 11.5 |

TABLE II-continued

| Example No. | A | $R^1$ | $R^2$ | $R^3$ | $R^4$ | Melting Point (°C.) | NMR δ ($d_6$-acetone)/ppm or Analysis (%) Calc. Found C | H | N |
|---|---|---|---|---|---|---|---|---|---|
| 40 | CH | $OCH_3$ | $OCH_3$ | $C_6H_5$ | (4-Cl)$C_6H_4$ | 166.0 | 37.5(6H, s), 5.61(1H, s), 5.88(1H, s), 7.28(3H, m), 7.30(2H, d), 7.57(2H, d), 7.64(2H, d) | | |
| 41 | CH | $CH_3$ | $CH_3$ | $CH_2C_6H_5$ | $CH_3$ | 96.0–98.0 | 55.0 / 54.6 | 5.5 / 5.4 | 12.0 / 11.8 |
| 42 | CH | $CH_3$ | $CH_3$ | $CH_2C_6H_5$ | $C_6H_5$ | 150.0 | 61.3 / 61.1 | 5.1 / 5.2 | 10.2 / 9.9 |
| 43 | CH | $OCH_3$ | $OCH_3$ | $iC_3H_7$ | $CH_3$ | 187.0 | 43.3 / 44.2 | 5.7 / 5.7 | 12.6 / 12.2 |
| 44 | CH | $OCH_3$ | $OCH_3$ | $iC_3H_7$ | $C_6H_5$ | 169.0–171.0 | 51.7 / 51.6 | 5.3 / 5.3 | 10.6 / 10.7 |
| 45 | N | $OCH_3$ | $OCH_3$ | $iC_3H_7$ | $C_6H_5$ | 162.1 | 48.5 / 49.7 | 5.1 / 5.3 | 14.1 / 14.1 |
| 46 | CH | $OCH_3$ | $OCH_3$ | $tC_4H_9$ | $CH_3$ | 153.0–154.0 | 45.0 / 45.0 | 6.1 / 6.1 | 12.1 / 12.2 |
| 47 | CH | $OCH_3$ | $OCH_3$ | $iC_4H_9$ | $CH_3$ | 163.0 | 45.0 / 45.4 | 6.1 / 6.2 | 12.1 / 12.4 |
| 48 | CH | $OCH_3$ | $OCH_3$ | $iC_4H_9$ | $C_6H_5$ | 53.0–55.0 | 52.8 / 53.2 | 5.6 / 5.9 | 10.3 / 9.9 |
| 49 | CH | $OCH_3$ | $OCH_3$ | $iC_4H_9$ | (4-$OCF_3$)$C_6H_4$ | 129.0–130.0 | 46.3 / 46.2 | 4.5 / 4.5 | 8.5 / 8.6 |
| 50 | CH | $OCH_3$ | $OCH_3$ | $nC_4H_9$ | $CH_3$ | 167.0–168.0 | 45.0 / 44.8 | 6.1 / 5.7 | 12.1 / 11.8 |
| 51 | CH | $OCH_3$ | $OCH_3$ | $nC_4H_9$ | $C_6H_5$ | 126.0–128.0 | 52.8 / 52.3 | 5.6 / 5.5 | 10.3 / 10.3 |
| 52 | CH | $OCH_3$ | $OCH_3$ | $nC_4H_9$ | (2-$CO_2CH_3$)$C_6H_4$ | 137.0 | 51.4 / 51.4 | 5.4 / 5.4 | 9.0 / 9.0 |
| 53 | CH | $CH_3$ | $CH_3$ | $C_2H_5$ | $CH_3$ | 167.0–169.0 | 46.0 / 45.3 | 5.9 / 5.8 | 14.6 / 14.3 |
| 54 | CH | $OCH_3$ | $OCH_3$ | $iC_3H_7$ | $C_2H_5$ | 158.0 | 45.0 / 45.4 | 6.1 / 6.1 | 12.1 / 12.2 |
| 55 | CH | $OCH_3$ | $OCH_3$ | $nC_4H_9$ | $iC_3H_7$ | 134.0 | 48.0 / 48.1 | 6.7 / 6.7 | 11.2 / 11.0 |
| 56 | CH | $OCH_3$ | $OCH_3$ | $CH_3$ | $nC_4H_9$ | 143.0–145.0 | 45.0 / 46.2 | 6.1 / 6.4 | 12.1 / 11.2 |
| 57 | N | $OCH_3$ | $OCH_3$ | $tC_4H_9$ | $CH_3$ | 153.5 | 41.3 / 41.9 | 5.7 / 6.2 | 16.1 / 16.1 |
| 58 | CH | $OCH_3$ | $OCH_3$ | $tC_4H_9$ | $nC_4H_9$ | 132.0 | 49.4 / 49.7 | 7.0 / 7.1 | 10.8 / 11.0 |
| 59 | CH | $OCH_3$ | $OCH_3$ | $C_6H_5$ | 2-thienyl | 155.0 | 49.7 / 49.9 | 3.9 / 3.9 | 9.7 / 9.6 |

EXAMPLE 60

2-(4,6-Dimethoxypyrimidin-2-yl)oxy-N-phenyl sulphonyl propionamide 0.12 g (0.0048 mol) of sodium hydride was added to the acyl sulphonamide HOCH($CH_3$)CONH-$SO_2C_6H_5$(0.50 g, 0.0022 mol) in 50 ml dimethyl formamide at room temperature (~20° C.) and stirred under a dry atmosphere for 40 minutes. 0.5 g (0.0022 mol) of 4,6-dimethoxy-2-methanesulphonyl-pyrimidine was then added which produced some effervescence. The reaction mixture was heated to 120° C. and maintained at that temperature for 1 hour. After this time, the dimethylformamide was evaporated off, the remaining liquid was diluted with water and acidified to a pH of 2; the product was then extracted into diethyl ether. Following drying and concentration and purification by flash column chromatography using 5% by volume methanol/chloroform, the title compound was obtained in the form of a brown oil (0.23 g, 0.0006 mol).

Yield: 28% by weight. Elemental Analysis (%):

| | Elemental Analysis (%) | | |
|---|---|---|---|
| Calculated | C 49.0 | H 4.6 | N 11.4 |
| Found | C 48.1 | H 5.0 | N 11.0 |

EXAMPLE 61

2-(4,6-Dimethoxytriazin-2-yl)oxy-N-phenylsulphonyl propionamide

2-Hydroxy N-phenylsulphonyl propionamide (1.50 g, 0.0066 mol) was dissolved in dry dioxan. Sodium hydride was added at ambient temperature and the mixture was stirred for 1 hour. The solution was Warmed to 50° C. for 20 min. 2-Chloro-4,6-dimethoxytriazine (1.15 g, 0.0066 mol) was added to the solution of disodium salt and the mixture refluxed for 2 hours.

The dioxan was evaporated off and the residue dissolved in water and extracted with ethyl acetate. The aqueous layer was then acidified to pH2 and extracted with ethyl acetate. The extracts were dried over $MgSO_4$ and the solvent evaporated to yield the title compound as a yellow oil (0.83 g, 0.0023 mol).

Yield: 34% by weight.

NMR δ($CDCl_3$):1.55(3H,d), 3.95(6H,s), 5.38(1H,q) 7.54(2H,t), 7.66(1H,t), 8.04(2H,d), 9.14(1H,s) ppm.

EXAMPLES 62 to 66

Further compounds of the general formula I were prepared in analogous manner to the procedure described in Example 61. Details of the prepared compounds are given in Table III below.

TABLE III

| Example No. | A | $R^1$ | $R^2$ | $R^3$ | $R^4$ | Melting Point (°C.) | NMR δ ($d_6$-acetone)/ppm or Analysis (%) Calc. Found | | |
|---|---|---|---|---|---|---|---|---|---|
| | | | | | | | C | H | N |
| 62 | CH | $CH_3$ | $CH_3$ | $C_6H_5$ | $C_6H_5$ | 195.0 | 60.5 | 4.8 | 10.6 |
| | | | | | | | 60.1 | 5.1 | 10.3 |
| 63 | CH | $OCH_3$ | Cl | $C_6H_5$ | $C_6H_5$ | 198.0 | 52.6 | 3.7 | 9.7 |
| | | | | | | | 52.1 | 4.0 | 9.5 |
| 64 | CH | $CH_3$ | $CH_3$ | $C_6H_5$ | $CH_3$ | 115.0–140.0 | 2.32(6H, s), 2.90(3H, br s), 6.08(1H, s), 6.83(1H, s), 7.35(3H, m), 7.61(2H, m) | | |
| 65 | CH | $OCH_3$ | Cl | $C_6H_5$ | $CH_3$ | 133.0–135.0 | 3.17(3H, s), 3.98(3H, s), 6.15(1H, s), 6.62(1H, s), 7.45(3H, m), 7.65(2H, m), 7.98(1H, s) | | |
| 66 | N | $OCH_3$ | $OCH_3$ | $C_6H_5$ | $CH_3$ | 119.0–120.0 | 3.21(3H, s), 3.97(6H, s), 6.21(1H, s), 7.44(3H, m), 7.62(2H, m), 10.96(1H, br s) | | |

EXAMPLE 67

Herbicidal Activity

To evaluate their herbicidal activity, compounds according to the invention were tested using as representative range of plants: maize, Zea mays (Mz); rice, Oryza sativa (R); barnyard grass, Echinochloa crusqalli (BG); oat, Avena sativa (O); linseed, Linum usitatissimum (L); mustard, Sinapsis alba (M); sugar beet, Beta vulgaris (SB) and soya bean, Glycine max (S).

The tests fall into two categories, pre-emergence and post-emergence. The pre-emergence tests involved spraying a liquid formulation of the compound onto the soil in which the seeds of the plant specied mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 litres per hectare in the soil spray and foliar spray test, and at a dosage of level equivalent to 10 kilograms of active material per hectare in a volume equivalent to approximately 3,000 litres per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table IV below, in which the compounds are identified by reference to the preceding examples. An asterisk in the following table indicates that no result was obtained; absence of a numeral indicates a zero rating.

TABLE IV

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1 | 7 | 7 | 6 | 7 | 4 | 8 | 8 | | 5 | 2 | 4 | 6 | 6 | 6 | 8 | 9 | 2 | 7 | 7 | 7 | 7 | 5 | 7 | 7 | 2 |
| | | | | | | | | | 1 | | 1 | 4 | 3 | 1 | 8 | 7 | | 3 | 2 | 5 | 2 | 1 | 6 | 5 | |
| 2 | | | | | 8 | 6 | 3 | | 5 | | | | 2 | 8 | 7 | 6 | | | | | | | 6 | 4 | |
| | | | | | | | | | 1 | | | | | 6 | | 2 | | | | | | | 5 | | |
| 3 | 2 | | 4 | | 2 | 8 | 7 | 2 | 5 | 2 | | 2 | 2 | 8 | 8 | 2 | | 1 | 5 | 5 | 3 | | 8 | 6 | |
| | | | | | | | | | 1 | | | 1 | 2 | 7 | 6 | | | | 2 | | 2 | | 6 | 3 | |
| 4 | | | 2 | | | 8 | 4 | | 5 | | 3 | | | 8 | 4 | 2 | | 3 | 4 | 5 | | | 7 | 3 | |
| | | | | | | | | | 1 | | | | | 7 | 2 | | | | | 1 | | | 7 | | |
| 5 | 7 | 7 | 7 | 3 | 2 | 8 | 5 | 2 | 5 | 5 | 2 | 7 | 4 | 4 | 8 | 8 | 6 | 7 | 8 | 8 | 4 | 3 | 7 | 8 | 3 |
| | | | | | | | | | 1 | 2 | | 5 | 1 | | 8 | 7 | 4 | 5 | 7 | 7 | 1 | | 7 | 6 | 2 |
| 6 | 3 | 2 | 6 | | | 8 | 3 | 2 | 5 | 2 | | 4 | | 1 | 7 | 6 | 5 | 3 | 4 | 6 | | | 6 | 4 | |
| | | | | | | | | | 1 | | | 1 | | | 7 | 3 | 1 | 1 | | 4 | | | 5 | 2 | |
| 7 | 7 | 7 | 8 | 4 | 4 | 8 | 9 | 5 | 5 | 7 | 6 | 7 | 4 | 7 | 8 | 8 | 7 | 8 | 9 | 8 | 7 | 8 | 7 | 8 | 7 |
| | | | | | | | | | 1 | 5 | 4 | 7 | 2 | 6 | 8 | 6 | 5 | 4 | 8 | 8 | 4 | 6 | 7 | 8 | 6 |
| 8 | 2 | 2 | 4 | | 4 | 7 | 2 | | 5 | | | | 4 | 8 | 2 | 3 | 4 | 4 | 4 | | 3 | 6 | 3 | |
| | | | | | | | | | 1 | | | | | 8 | | 2 | | | | | | | 5 | 2 | |
| 9 | 6 | 4 | 4 | 2 | 2 | 7 | 3 | 3 | 5 | 2 | | 4 | | 5 | 7 | 7 | 3 | 4 | | | | | 4 | | |
| | | | | | | | | | 1 | | | 4 | | | 6 | 4 | 1 | 1 | | | | | 3 | | |

TABLE IV-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 10 | | | | | | 5 | 3 | | 5 | | | 3 | | 2 | 7 | 6 | 3 | 2 | | 3 | | | 5 | 3 | |
| | | | | | | | | | 1 | | | 2 | | | 7 | 4 | | 1 | | | | | 3 | 1 | |
| 11 | 2 | 3 | 4 | | 2 | 7 | 3 | 3 | 5 | | | 4 | | | 7 | 5 | 4 | 4 | 3 | 4 | | | 7 | 4 | 6 |
| | | | | | | | | | 1 | | | 3 | | | 6 | 2 | 2 | 1 | | 1 | | | 5 | 2 | |
| 12 | | | | | 3 | 5 | | | 5 | | | 2 | | 3 | 7 | 3 | 2 | | | | | | 5 | | |
| | | | | | | | | | 1 | | | | | | 5 | | | | | | | | 3 | | |
| 13 | | | | | 2 | 6 | 5 | | 5 | | | 2 | | 3 | 7 | 4 | | 3 | | | | | 6 | 6 | |
| | | | | | | | | | 1 | | | | | | 5 | 2 | | | | | | | 6 | | |
| 14 | | | | | | 6 | 3 | | 5 | | | 2 | | 3 | 7 | 5 | 2 | | | 2 | | | 5 | | |
| | | | | | | | | | 1 | | | | | | 6 | 4 | 1 | | | 1 | | | 4 | | |
| 15 | | 4 | 6 | | | 8 | 3 | | 5 | 2 | | 6 | | 3 | 8 | 3 | 2 | 1 | | 6 | | | 7 | 5 | |
| | | | | | | | | | 1 | | | 3 | | | 7 | | 1 | | | 2 | | | 4 | | |
| 16 | 2 | 4 | 5 | 3 | 2 | 7 | 5 | 3 | 5 | | | 3 | 2 | 3 | 7 | 5 | 2 | 4 | 4 | 6 | 2 | 2 | 7 | 3 | |
| | | | | | | | | | 1 | | | | 1 | | 7 | 2 | | 2 | 1 | 2 | 1 | | 7 | 1 | |
| 17 | 2 | | 2 | | 3 | 7 | 2 | 2 | 5 | | | 2 | | 2 | 6 | 2 | 3 | | | 3 | | | 6 | 2 | |
| | | | | | | | | | 1 | | | | | | 5 | | | | | | | | 4 | | |
| 18 | 5 | 5 | 7 | 3 | 2 | 8 | 7 | | 5 | 3 | 2 | 7 | 5 | 3 | 8 | 7 | 3 | 7 | 8 | 8 | 4 | | 7 | 7 | 2 |
| | | | | | | | | | 1 | 2 | 1 | 5 | 2 | | 8 | 6 | 1 | 4 | 4 | 7 | 2 | | 7 | 5 | |
| 19 | 4 | 7 | 4 | 2 | 8 | 2 | 2 | | 5 | | | 7 | 3 | 3 | 8 | 7 | 4 | 7 | 6 | 7 | 2 | | 8 | 6 | |
| | | | | | | | | | 1 | | | 2 | 1 | 1 | 8 | 4 | 2 | 2 | | 3 | 1 | | 8 | 2 | |
| 20 | 2 | 1 | 2 | | 3 | 8 | 5 | 4 | 5 | | | 2 | | 4 | 8 | 6 | 4 | 4 | 4 | 3 | | 2 | 8 | 3 | |
| | | | | | | | | | 1 | | | | | 1 | 7 | 2 | 1 | | | | | | 7 | 1 | |
| 21 | 6 | 6 | 8 | | | 8 | 7 | 4 | 5 | 4 | 3 | 7 | 3 | 2 | 8 | 6 | 5 | 7 | 7 | 7 | | | 8 | 6 | |
| | | | | | | | | | 1 | 1 | | 2 | 1 | | 8 | 4 | 2 | 5 | 3 | 5 | | | 8 | 4 | |
| 22 | | | | | 2 | 4 | | | 5 | 2 | | 2 | 2 | 3 | 8 | 4 | | | | | | | 3 | | |
| | | | | | | | | | 1 | 1 | | | | | 7 | 3 | | | | | | | | | |
| 23 | 7 | 6 | 8 | 7 | 3 | 9 | 8 | | 5 | 6 | 3 | 7 | 6 | 3 | 8 | 7 | 5 | 8 | 8 | 8 | 6 | 4 | 7 | 7 | 3 |
| | | | | | | | | | 1 | 3 | | 5 | 3 | 1 | 8 | 7 | 3 | 7 | 6 | 7 | 3 | | 7 | 7 | |
| 24 | 4 | 4 | 8 | 4 | 7 | 9 | 8 | 5 | 5 | 4 | 2 | 3 | 2 | 4 | 8 | 7 | 8 | 6 | 6 | 7 | 5 | 8 | 8 | 8 | 7 |
| | | | | | | | | | 1 | 1 | | 1 | 1 | | 8 | 7 | 7 | | 2 | 5 | | 7 | 8 | 8 | 6 |
| 25 | | 3 | 2 | 3 | 2 | 6 | 3 | 2 | 5 | 2 | | 2 | 4 | 3 | 7 | 2 | 3 | | 5 | 2 | 6 | | 4 | 2 | |
| | | | | | | | | | 1 | | | | 2 | 2 | 6 | | 1 | | 4 | | 6 | | 4 | | |
| 26 | 8 | 8 | 8 | 4 | 3 | 8 | 5 | 6 | 5 | 7 | 8 | 8 | 7 | 7 | 8 | 8 | 8 | 8 | 9 | 9 | 6 | 8 | 7 | 8 | 7 |
| | | | | | | | | | 1 | 3 | 7 | 7 | 6 | 7 | 8 | 8 | 7 | 5 | 8 | 8 | 3 | 6 | 7 | 7 | 6 |
| 27 | 8 | 8 | 7 | 5 | 6 | 8 | 6 | 7 | 5 | 5 | 8 | 8 | 6 | 7 | 8 | 8 | 8 | 8 | 8 | 9 | 5 | 7 | 7 | 7 | 7 |
| | | | | | | | | | 1 | 3 | 8 | 8 | 5 | 7 | 8 | 8 | 8 | 5 | 6 | 8 | 2 | 5 | 7 | 5 | 3 |
| 28 | | | | | | 7 | 4 | | 5 | | | | | | 5 | 7 | 3 | | | | | | | | |
| | | | | | | | | | 1 | | | | | | 1 | 6 | | | | | | | | | |
| 29 | 6 | 5 | 6 | 3 | 2 | 8 | 6 | | 5 | 1 | | 5 | 1 | 5 | 8 | 8 | 7 | 5 | 5 | 8 | 3 | 3 | 7 | 6 | 3 |
| | | | | | | | | | 1 | | | 2 | | | 7 | 6 | | 2 | 3 | 6 | 1 | | 2 | 2 | |
| 30 | 2 | 4 | 6 | 2 | 4 | 8 | 5 | | 5 | 3 | | 5 | 3 | 5 | 8 | 8 | 2 | 5 | 3 | 5 | 4 | 5 | 7 | 6 | 4 |
| | | | | | | | | | 1 | 2 | | 2 | 1 | 1 | 7 | 5 | | 2 | | 3 | 1 | | 7 | 4 | |
| 31 | 7 | 7 | 7 | 7 | 4 | 8 | 6 | 5 | 5 | 5 | 3 | 7 | 6 | 6 | 8 | 8 | 5 | 7 | 7 | 7 | 7 | 6 | 7 | 8 | 7 |
| | | | | | | | | | 1 | 2 | 1 | 6 | 4 | 3 | 7 | 6 | 5 | 4 | 3 | 4 | 5 | 3 | 7 | 5 | 5 |
| 32 | | | 2 | | | 7 | 4 | | 5 | 2 | | | | 3 | 8 | 5 | 3 | 5 | 4 | 5 | 4 | 4 | 7 | 8 | 4 |
| | | | | | | | | | 1 | | | | | | 6 | 3 | 1 | 1 | 1 | 2 | 1 | | 2 | 4 | 1 |
| 33 | 2 | | 2 | | | 6 | 3 | | 5 | 2 | | 2 | 1 | 3 | 7 | 6 | 4 | 3 | 3 | 3 | 2 | 6 | 5 | 5 | 2 |
| | | | | | | | | | 1 | | | | | | 7 | 4 | 2 | | | | | | 2 | 3 | 1 |
| 34 | | | 3 | | | 6 | 5 | 4 | 5 | 4 | | 5 | 2 | 5 | 8 | 8 | 6 | 4 | 4 | 6 | | 5 | 5 | 6 | 3 |
| | | | | | | | | | 1 | 2 | | 1 | | 1 | 6 | 3 | 3 | | | 2 | | 2 | 1 | 2 | 1 |
| 35 | 2 | 3 | 4 | 2 | | 6 | 4 | 4 | 5 | 3 | 2 | 7 | 3 | 6 | 8 | 8 | 4 | 3 | | 7 | 3 | 4 | 6 | 6 | |
| | | | | | | | | | 1 | 1 | | 4 | 1 | | 6 | 4 | 3 | 1 | | 5 | 1 | | 2 | 4 | |
| 36 | 2 | 5 | 3 | 2 | | 7 | 4 | 5 | 5 | 1 | 5 | 8 | 4 | 5 | 8 | 4 | 2 | 3 | 5 | 6 | 4 | 5 | 7 | 7 | 2 |
| | | | | | | | | | 1 | | 1 | 6 | 1 | 3 | 7 | 7 | 2 | | 1 | 3 | 1 | | 2 | 5 | |
| 37 | 2 | 6 | 4 | 1 | | 7 | 4 | 3 | 5 | 4 | 6 | 7 | 5 | 6 | 8 | 7 | 3 | 2 | 4 | 7 | 4 | 2 | 6 | 7 | 4 |
| | | | | | | | | | 1 | | 4 | 6 | 2 | 3 | 6 | 7 | 2 | | 2 | 6 | 1 | | 1 | 5 | |
| 38 | | | | | | 6 | 4 | 2 | 5 | | | | | | 6 | | | 2 | | 3 | 2 | | 2 | | 2 |
| | | | | | | | | | 1 | | | | | | 6 | | | | | 1 | 1 | | | | |
| 39 | | | 2 | | | | 4 | | 5 | 2 | | 4 | | | 6 | 2 | 2 | | | 2 | | | 3 | 5 | |
| | | | | | | | | | 1 | | | | | | 3 | 1 | 1 | | | | | | 1 | | |
| 40 | | | | | | 3 | 4 | | 5 | 4 | | | | 2 | 2 | 8 | 3 | 3 | | | | | 3 | 3 | |
| | | | | | | | | | 1 | | | | | | 5 | | 1 | | | | | | 1 | 2 | |
| 41 | | | | | | 8 | 3 | | 5 | | | 3 | 2 | | 8 | 5 | | | | | | | 6 | | |
| | | | | | | | | | 1 | | | 2 | 1 | | 7 | 2 | | | | | | 2 | | | |
| 42 | | | | 3 | 3 | 8 | 4 | | 5 | 2 | | 4 | | | 8 | 3 | | | | | | 2 | 7 | 3 | 4 |
| | | | | | | | | | 1 | | | | | | 7 | | | | | | | 1 | 5 | | |
| 43 | 7 | 7 | 8 | 7 | 6 | 8 | 8 | 7 | 5 | 7 | 7 | 8 | 7 | 7 | 8 | 8 | 6 | 8 | 9 | 9 | 7 | 8 | 7 | 8 | 6 |
| | | | | | | | | | 1 | 6 | 7 | 7 | 7 | 6 | 8 | 7 | 5 | 6 | 8 | 8 | 6 | 7 | 7 | 6 | 6 |
| 44 | 1 | 8 | 6 | 6 | 3 | 8 | 4 | 4 | 5 | | 6 | 7 | 5 | 4 | 8 | 5 | 5 | 5 | 6 | 7 | 6 | 5 | 8 | 5 | 2 |
| | | | | | | | | | 1 | | 3 | 2 | | | 7 | 3 | 2 | 1 | 2 | 2 | 3 | 1 | 7 | 2 | 2 |
| 45 | | | | | | 3 | 3 | 2 | 5 | 4 | 3 | 5 | 6 | 5 | 7 | 5 | 5 | * | * | * | * | * | * | * | * |
| | | | | | | | | | 1 | 1 | 3 | 5 | 6 | 3 | 6 | * | | 4 | 3 | 5 | 6 | 2 | 2 | 5 | |
| 46 | 7 | 7 | 8 | 7 | 6 | 8 | 8 | 7 | 5 | 8 | 6 | 8 | 6 | 7 | 9 | 8 | 8 | 8 | * | 8 | 8 | 7 | 8 | 8 | 8 |
| | | | | | | | | | 1 | 7 | 6 | 8 | 6 | 6 | 9 | 8 | 8 | 8 | * | 8 | 7 | 7 | 8 | 6 | |
| 47 | 3 | 6 | 6 | 5 | 6 | 7 | 8 | 5 | 5 | 5 | 5 | 7 | 6 | 6 | 8 | 8 | 6 | 6 | 7 | 8 | 6 | 6 | 6 | 6 | 3 |
| | | | | | | | | | 1 | 2 | 4 | 6 | 5 | 4 | 7 | * | 4 | 5 | 6 | 8 | 3 | 3 | 6 | 6 | 1 |
| 48 | | 7 | 7 | 5 | 2 | 7 | 7 | 7 | 5 | 3 | | 5 | | | 8 | 7 | 5 | | | | | | | | |
| | | | | | | | | | 1 | | | 2 | | | 8 | 4 | 4 | | | | | | | | |

TABLE IV-continued

| Compound of Ex. No | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 49 | | 6 | 4 | | | 2 | 5 | 6 | 5 | | | | | | 6 | 2 | 6 | 3 | 6 | 7 | 6 | | | 3 | 7 |
| | | | | | | | | | 1 | | | | | | | 2 | | | | | | | | | 2 |
| 50 | 4 | 8 | 8 | 6 | 4 | 8 | 8 | 6 | 5 | 2 | 7 | 8 | 3 | 5 | 9 | 8 | 4 | 4 | 5 | 7 | 6 | 8 | 8 | 8 | 6 |
| | | | | | | | | | 1 | | 6 | 8 | 1 | 3 | 8 | 7 | 3 | | 5 | 3 | 3 | | 8 | 6 | |
| 51 | 4 | 8 | 8 | 7 | 6 | 8 | 7 | 6 | 5 | 3 | 7 | 8 | 6 | 6 | 8 | 8 | 6 | 4 | 6 | 9 | 8 | 6 | 8 | 7 | 8 |
| | | | | | | | | | 1 | | 5 | 7 | 1 | 3 | 8 | 6 | 2 | 2 | 3 | 6 | 7 | 5 | 7 | 7 | 7 |
| 52 | 4 | 7 | 7 | 6 | 5 | 8 | 7 | 6 | 5 | | 3 | 7 | 2 | 5 | 8 | 8 | 6 | 8 | 7 | 9 | 6 | 2 | 6 | 7 | 7 |
| | | | | | | | | | 1 | | | 4 | | 1 | 7 | 6 | 4 | 4 | 3 | 6 | 5 | | 6 | 6 | 2 |
| 53 | | | | | 7 | 5 | | | 5 | | | 5 | 2 | | 9 | 6 | | | | | | | | | |
| | | | | | | | | | 1 | | | 1 | | | 7 | 5 | | | | | | | | | |
| 54 | 7 | 8 | 8 | 7 | 8 | 8 | 8 | 7 | 5 | 4 | 8 | 8 | 7 | 8 | 9 | 8 | 5 | 7 | 8 | 5 | 8 | 8 | 8 | 8 | 7 |
| | | | | | | | | | 1 | 4 | 7 | 7 | 5 | 7 | 8 | 8 | 3 | 3 | 5 | 3 | 4 | 3 | 4 | * | 4 |
| 55 | | 7 | 6 | 5 | 6 | 8 | 8 | 4 | 5 | 3 | 5 | 6 | 4 | 7 | 9 | 8 | 5 | 7 | 7 | 6 | 7 | 8 | 8 | 8 | 2 |
| | | | | | | | | | 1 | 1 | 3 | 4 | 1 | 5 | 8 | 7 | | 5 | 3 | | 5 | 5 | 8 | 7 | |
| 56 | | | | | | 6 | 4 | | 5 | | | | | | 4 | 6 | | | | | | | | | |
| | | | | | | | | | 1 | | | | | | | 2 | | | | | | | | | |
| 57 | 8 | 7 | 7 | 8 | 7 | 9 | 8 | 7 | 5 | 8 | 7 | 9 | 8 | 8 | 8 | 8 | 8 | 9 | 8 | 9 | 8 | 8 | 8 | 8 | 8 |
| | | | | | | | | | 1 | 3 | 4 | 8 | 7 | 7 | 8 | 7 | 7 | 9 | 5 | 8 | 7 | 7 | 8 | 3 | 7 |
| 58 | 8 | 7 | 9 | 7 | 8 | 9 | 8 | 8 | 5 | 5 | 6 | 8 | 6 | 7 | 9 | 8 | 7 | 7 | 8 | 8 | 8 | 8 | 8 | 8 | 5 |
| | | | | | | | | | 1 | 3 | 5 | 7 | 2 | 6 | 8 | 8 | 6 | 5 | 5 | 7 | 6 | 6 | 8 | 6 | 2 |
| 59 | 2 | 5 | 5 | 3 | 5 | 8 | 5 | 3 | 5 | 2 | | | | 1 | 8 | 7 | 6 | | 5 | 6 | | 3 | 8 | 8 | 6 |
| | | | | | | | | | 1 | | | | | | 8 | 5 | 1 | | | | | | | 7 | 7 |
| 60 | * | * | * | * | * | * | * | * | 5 | | | 4 | | 3 | 8 | 7 | 3 | 3 | 6 | 6 | 2 | 5 | 7 | 7 | |
| | | | | | | | | | 1 | * | * | * | * | * | * | * | * | * | * | * | * | * | * | * | * |
| 61 | 2 | | | 2 | | 7 | 4 | | 5 | 7 | 4 | 7 | 5 | 7 | 7 | 7 | 7 | * | * | * | * | * | * | * | * |
| | | | | | | | | | 1 | 7 | 4 | 7 | 5 | 6 | 7 | 7 | 7 | 7 | 7 | 6 | 3 | 4 | 6 | 3 | 3 |
| 62 | 2 | 4 | 4 | | | 7 | 5 | 4 | 5 | 2 | 2 | 3 | 3 | 2 | 8 | 7 | 4 | | 4 | 5 | 4 | | 7 | 6 | 8 |
| | | | | | | | | | 1 | | | 1 | | | 7 | 4 | 3 | | 1 | 2 | 1 | | 3 | 2 | 2 |
| 63 | 4 | 6 | 5 | | 2 | 7 | 6 | 3 | 5 | 4 | | 5 | 4 | 6 | 8 | 8 | 6 | 4 | 4 | 6 | 2 | 5 | 7 | 6 | |
| | | | | | | | | | 1 | 1 | | 2 | 3 | 4 | 7 | 7 | 4 | 1 | 2 | 2 | | 2 | 4 | 2 | |
| 64 | 7 | 7 | 7 | 7 | | 7 | 6 | 2 | 5 | 4 | 6 | 8 | 7 | 3 | 8 | 8 | 5 | 7 | 9 | 9 | 7 | 2 | 7 | 7 | 3 |
| | | | | | | | | | 1 | 1 | 3 | 7 | 5 | | 7 | 7 | 2 | 4 | 8 | 7 | 5 | | 6 | 6 | 3 |
| 65 | * | * | * | * | * | * | * | * | 5 | 2 | | 6 | 2 | 2 | 7 | 4 | 3 | 6 | 6 | 7 | 3 | 2 | 5 | 5 | |
| | | | | | | | | | 1 | * | * | * | * | * | * | * | * | * | * | * | * | * | * | * | * |
| 66 | | | | | | | | | 5 | 4 | | 7 | 5 | | 7 | 3 | 2 | 4 | 5 | 4 | 2 | | 2 | 2 | 3 |
| | | | | | | | | | 1 | | | | | | 1 | 6 | | | | | | | | | |

We claim:

1. A compound of the formula

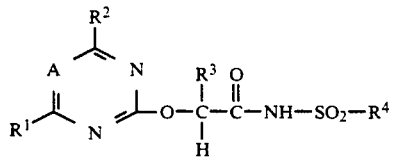

(I)

in which

A represents a group $CR^5$;

$R^1$, $R^2$ and $R^5$ each independently represents a hydrogen or halogen atom, a formyl, cyano, carboxy or azido group, or an optionally substituted $C_{1-12}$ alkyl, $C_{2-12}$ alkenyl, $C_{2-12}$ alkynyl, $C_{3-8}$ cycloalkyl, $C_{1-12}$ alkoxy, $C_{2-12}$ alkenyloxy, $C_{2-12}$ alkynyloxy, aryloxy, $C_{1-12}$ alkylthio, $C_{2-12}$ alkenylthio, $C_{2-12}$ alkynylthio, arylthio, $C_{1-12}$ alkylcarbonyl, $C_{1-12}$ alkoxycarbonyl, amino, aminoxy or $C_{1-12}$ dialkyliminoxy group;

$R^3$ represents a hydrogen atom, or an optionally substituted $C_{1-12}$ alkyl, $C_{2-12}$ alkenyl, $C_{2-12}$ alkynyl, $C_{3-8}$ cycloalkyl, heterocyclic, aralkyl or aryl group; and $R^4$ represents an optionally substituted $C_{1-12}$ alkyl, aralkyl, aryl or heterocyclic group; or a salt thereof, optional substituents for alkyl, alkenyl, alkynyl, alkoxy, alkenyloxy, alkynyloxy, alkylthio, alkenylthio, alkynylthio, alkylcarbonyl, alkoxycarbonyl groups or alkyl moieties in aralkyl groups being independently selected from one or more of halogen atoms and $C_{1-12}$ alkoxy, $C_{2-12}$ alkenyloxy, aryloxy, hydroxy, $C_{1-12}$ alkylthio, arylthio, aryl, $C_{1-12}$ alkylsulphonyl, $C_{2-12}$ alkylsulphinyl, $C_{1-12}$ alkylenedioxy, $C_{1-12}$ alkylenedithio, halo-$C_{1-12}$ alkyl and $C_{1-12}$ alkoxycarbonyl groups, heterocyclic groups, and di-$C_{1-12}$ alkyliminoxy, optionally substituted amino, trialkylsilyl, $C_{1-12}$ alkylcarbonyl, arylcarbonyl, $C_{1-12}$ alkoxycarbonyl, carboxy, cyano, thiocycanato and optionally substituted aminocarbonyl groups, optional substituents for aryl, cycloalkyl, aryloxy or arylthio groups, heterocyclic rings or aryl moieties in aralkyl groups being independently selected from one or more of halogen atoms and nitro, cyano, $C_{1-12}$ alkyl, halo-$C_{1-12}$ alkyl, $C_{1-12}$ alkoxy, halo-$C_{1-12}$ alkoxy, $C_{1-12}$ alkylthio, $C_{1-12}$ alkylsulphonyl, mono- or di-$C_{1-12}$ alkylsulphonamido, aryloxy, carboxy, $C_{1-12}$ alkoxycarbonyl and aralkoxycarbonyl groups, and optional substituents for an amino group or for an amino moiety in an aminoxy or aminocarbonyl group, being selected from $C_{1-12}$ alkyl, $C_{2-12}$ alkenyl, aryl, $C_{1-12}$ alkoxy, amino, mono- or di-$C_{1-12}$ alkylamino, arylamino, $C_{1-12}$ alkoxyalkyl, halo-$C_{1-12}$ alkyl, hydroxy, hdyroxy-$C_{1-12}$ alkyl, cyano, carboxy-$C_{1-12}$ alkyl or $C_{1-12}$ alkylcarbonylamino, or the amino group may form part of a heterocyclic ring, said aryl radical and said aryl moiety of said aralkyl, aryloxy, or arylthio radicals comprising a single or fused carbocyclic ring system having 6-10 ring carbon atoms, and said heterocyclic radical comprising a single ring system having from 5 to 6 ring members of which one is a hetero atom selected from oxygen, nitrogen, and sulphur.

2. A compound as claimed in claim 12, in which A represents a group CH.

3. A compound as claimed in claim 13, in which each of $R^1$ and $R^2$ independently represents a chlorine atom or a $C_{1-14}$ alkyl or $C_{1-4}$ alkoxy group.

4. A compound as claimed in claim 13, in which $R^3$ represents a hydrogen atom or a $C_{1-6}$ alkyl, phenyl or benzyl group.

5. A compound as claimed in claim 13, in which $R^4$ represents a $C_{1-6}$ alkyl group, a benzyl group, a thienyl group, or a phenyl group which is unsubstituted or substituted by one or more of the same or different substituents selected from halogen atoms, nitro groups, $C_{1-4}$ alkyl groups, $C_{1-4}$ haloalkyl groups, $C_{1-4}$ haloalkoxy groups, carboxy groups, and ($C_{1-4}$ alkoxy)carbonyl groups.

6. A compound as claimed in claim 13, in which A represents a group CH, $R^1$ and $R^2$ are the same and each represents a methyl or a methoxy group, $R^3$ represents a hydrogen atom, a $C_{1-4}$ alkyl group or a phenyl group, and $R^4$ represents a $C_{1-4}$ alkyl group or a phenyl group which is unsubstituted or substituted by a fluorine, chlorine or bromine atom or a nitro, methyl, trichloromethyl, trifluoromethoxy or methoxycarbonyl group.

7. A method of combating undesired plant growth of a locus which comprises treating the locus with an effective compound of a compound as claimed in claim 13.

8. A herbicidal composition which comprises an effective amount of compound as claimed in claim 13, in association with at least one carrier.

9. A method of combating undesired plant growth of a locus which comprises treating the locus with a composition as claimed in claim 8.

* * * * *

UNITED STATES PATENT AND TRADEMARK OFFICE
CERTIFICATE OF CORRECTION

PATENT NO. : 5,158,599

DATED : October 27, 1992

INVENTOR(S) : DAVID P. ASTLES ET AL.

It is certified that error appears in the above-identified patent and that said Letters Patent is hereby corrected as shown below:

Col. 20, claim 1, line 41 of the claim, "$C_{2-12}$ alkylsulphinyl" should read --$C_{1-12}$ alkylsulphinyl--;

line 63 of the claim, "hdyroxy-$C_{1-12}$ alkyl" should read --hydroxy-$C_{1-12}$ alkyl--.

Col. 21, claim 2, line 1 of the claim, "12" should read --1--.
claim 3, line 1 of the claim, "13" should read --1--;

line 3 of the claim, "$C_{1-14}$" should read --$C_{1-4}$--.
claims 4, 5 and 6, line 1 of the claims, "13" should read --1--.

Col. 22, claim 7, line 1 of the claim, "of" should read --at--;

line 3 of the claim, "compound" (first occurrence) should read --amount--;

line 4 of the claim, "13" should read --1--.
claim 8, line 2 of the claim, "13" should read --1--.

Signed and Sealed this

Second Day of November, 1993

BRUCE LEHMAN

*Attest:*

*Attesting Officer*      Commissioner of Patents and Trademarks